(12) United States Patent
Chudoba et al.

(10) Patent No.: US 7,316,155 B2
(45) Date of Patent: Jan. 8, 2008

(54) TEST TABLE FOR MEASURING LATERAL FORCES AND DISPLACEMENTS

(75) Inventors: Thomas Chudoba, Dresden (DE); Norbert Schwarzer, Eilenburg (DE); Ilja Hermann, Lössnitz (DE)

(73) Assignee: ASMEC Advanced Surface Mechanics GmbH, Radeberg (DE)

( * ) Notice: Subject to any disclaimer, the term of this patent is extended or adjusted under 35 U.S.C. 154(b) by 124 days.

(21) Appl. No.: 10/532,630
(22) PCT Filed: Oct. 23, 2003
(86) PCT No.: PCT/DE03/03556

§ 371 (c)(1),
(2), (4) Date: Sep. 7, 2005

(87) PCT Pub. No.: WO2004/040265

PCT Pub. Date: May 13, 2004

(65) Prior Publication Data

US 2006/0096387 A1    May 11, 2006

(30) Foreign Application Priority Data

Oct. 24, 2002    (DE) .............................. 102 49 767

(51) Int. Cl.
*B23Q 16/00* (2006.01)
*G01N 3/48* (2006.01)
(52) U.S. Cl. .......................................... 73/81; 33/568
(58) Field of Classification Search .................. 73/849, 73/81; 33/568
See application file for complete search history.

(56) References Cited

U.S. PATENT DOCUMENTS

| | | | |
|---|---|---|---|
| 2,573,286 A | 10/1951 | Baker et al. | |
| 3,201,980 A | 8/1965 | Webb | |
| 3,982,738 A * | 9/1976 | Meier et al. | 267/121 |
| 4,157,818 A | 6/1979 | Key | |
| 4,635,887 A * | 1/1987 | Hall et al. | 248/179.1 |
| 4,925,139 A * | 5/1990 | McCord | 248/176.3 |
| 5,051,594 A | 9/1991 | Tsuda et al. | |

(Continued)

FOREIGN PATENT DOCUMENTS

WO    WO 99 46576    9/1999

(Continued)

OTHER PUBLICATIONS

"Microscratch and Load Relaxation Tests for Ultra-Thin Films"—Wu T. W. Journal of Materials Research, New York, NY, U.S., vol. 6, No. 2, pp. 407-426 Feb. 1991.

(Continued)

*Primary Examiner*—Michael Cygan
*Assistant Examiner*—Jonathan Dunlap
(74) *Attorney, Agent, or Firm*—Collard & Roe, P.C.

(57) ABSTRACT

A test table for measuring lateral forces and displacements while simultaneously applying, if necessary, normal forces, particularly in nanoidenters and in scratch and wear testers. The test table is mounted in a manner that enables it to be laterally displaced, and the lateral force and displacement can be determined by means of a measured-value acquisition. The test table is fixed between at least two vertically upright leaf springs, which can be laterally deflected in the direction of the lateral (horizontal) motion of the test table to be effected.

10 Claims, 2 Drawing Sheets

U.S. PATENT DOCUMENTS

| | | | |
|---|---|---|---|
| 5,067,346 A * | 11/1991 | Field | 73/81 |
| 5,232,062 A * | 8/1993 | Neuman | 177/187 |
| 5,343,748 A | 9/1994 | Mozgowiec et al. | |
| 5,360,974 A * | 11/1994 | Hammond et al. | 250/442.11 |
| 5,523,941 A * | 6/1996 | Burton et al. | 700/60 |
| 5,854,487 A * | 12/1998 | Braunstein et al. | 250/306 |
| 5,999,887 A * | 12/1999 | Giannakopoulos et al. | 702/33 |
| 6,246,052 B1 * | 6/2001 | Cleveland et al. | 250/234 |
| 6,520,004 B1 * | 2/2003 | Lin | 73/81 |

FOREIGN PATENT DOCUMENTS

WO    WO 02 16907    2/2002

OTHER PUBLICATIONS

International Search Report.

"Microscratch and Load Relaxation Tests for Ultra-Thin Films"—Wu T. W. Journal of Materials Research, New York, NY, U.S., vol. 6, No. 2, pp. 407-426 Feb. 1991, enclosed May 12, 2006.

"Microscratch and Load Relaxation Tests for Ultra-Thin Films"—Wu T. W. Journal of Materials Research, New York, NY, U.S., vol. 6, No. 2, pp 407-426 Feb. 1991, (to follow).

* cited by examiner

TEST TABLE FOR MEASURING LATERAL FORCES AND DISPLACEMENTS

CROSS REFERENCE TO RELATED APPLICATIONS

Applicants claim priority under 35 U.S.C. §119 of German Application No. 102 49 767.2 filed Oct. 24, 2002. Applicants also claim priority under 35 U.S.C. §365 of PCT/DE2003/003556 filed Oct. 23, 2003. The international application under PCT article 21(2) was not published in English.

BACKGROUND OF THE INVENTION

1. Field of the Invention

The invention relates to a test table for measuring lateral forces and displacements.

Measurement of the lateral forces and displacements takes place with the simultaneous application of normal forces, and is used, in particular, in nano-indenters as well as in scratch and wear testers.

In the case of these devices, a normal force is usually applied to a sample to be tested, by way of a diamond testing body, and the displacement caused by the normal force is measured. In addition, the test table is moved laterally under the test body, to achieve a relative movement. The force required for this and the size of the lateral displacement are measured.

2. Prior Art

WO 02/16907 A1 describes a device for testing scratch resistance (scratch tester). The test table is mounted to be tangentially movable, whereby the mobility is achieved by means of two C-shaped bend parts that are provided with notches on the inside edges, in each instance. The tangential force exerted on the sample by the scratch tool is detected on the test table by way of a measured-value transducer. WO 99/46576 relates to a device for measuring the scratch resistance of coatings (scratch tester), which possesses an indenter part and a test table. The test table consists of a clamping device for the sample, which is attached to an I-shaped block, which in turn was affixed to a holder device block by way of four horizontally oriented membrane springs, making the sample laterally movable. The tangential forces are detected by way of a sensor, while the indenter tip is drawn over the sample surface. As this happens, the springs are not subject to tensile bias. Furthermore, the leaf spring longitudinal direction extends horizontally and not vertically in the direction of the normal force, resulting in a less advantageous system of action.

SUMMARY OF THE INVENTION

It is the task of the invention to conceive a test table with which normal force and displacement as well as lateral force and displacement can be measured with great accuracy, independent of one another, in each instance, whereby the test table itself does not cause any displacements, even when great normal forces are in effect.

This task is accomplished with the characterizing features of the first claim; advantageous further developments are evident from the dependent claims.

The test table for measuring lateral forces and displacements, with the simultaneous application of normal forces, if necessary, particularly in nano-indenters as well as scratch and wear testers, is mounted to be movable laterally, whereby the lateral force and displacement can be determined by way of a measured-value acquisition. According to the invention, the test table is attached between at least two leaf springs that extend perpendicular in the longitudinal direction of the leaf spring and can be deflected laterally in the direction of the lateral (horizontal) movement of the test table that is to be produced.

In this connection, the leaf springs are attached to a frame, preferably under bias, at their lower end and at their upper end. Between the lower end and the upper end of the leaf springs, the test table is suspended on them, e.g. at specific points. In this connection, the arrangement of the test table takes place preferably in the center of the leaf springs, whereby two leaf springs stand opposite one another as a pair of leaf springs. In this connection, it is also possible to mount the test table between several pairs of leaf springs.

The thickness of the leaf springs should be greater than/ equal to their lateral deflection, in order to maintain linearity. It is furthermore advantageous if the test table is connected with a damping unit. An oil bath preferably disposed below the test table is used for this purpose, and a damping element disposed on the test table dips into this bath. This damping unit is to be sized in such a manner that vibrations that come from the surroundings, in particular, are effectively damped, without any noticeable influence on the desired lateral movement of the table.

The sample holder is designed to be movable laterally, in order to be able to set the sample surface to the same height even when the thickness of the samples varies.

The measured-value acquisition has a shaft that detects a value close to the sample, to determine the lateral force and displacement. This shaft is attached vertically in the region between the center of the springs and the sample surface, as well as vertically precisely in the center of the sample holder, and serves to displace the table in the lateral direction as well as to measure this displacement. The shaft can also be mounted on spring elements, and the lateral force can be determined directly from their deflection. Measurement of the displacement of the shaft takes place using suitable measurement means (e.g. LVDTs).

Dynamic measurements are also possible, by means of a cyclic displacement of the table in the lateral direction. Tribological contacts can be simulated in this manner, e.g. of gear wheels during their movement. The vibrations from the surroundings are reduced by means of the damping unit disposed below the test table.

The measured-value acquisition to determine the lateral force and displacement can also take place optically.

The solution according to the invention preferably provides for four leaf springs that stand perpendicular opposite one another, which are attached to a frame under tensile stress. The test table is attached in the center of the leaf springs, at specific points. As a result, a very great normal rigidity and torsion rigidity of the frame and the test table are achieved.

The test table is therefore suspended in the center of the leaf springs, resulting in the creation of a new and improved type of a principle of effect, which is characterized by great torsion rigidity and normal rigidity of both the frame and the test table.

The main advantage of the invention consists in the fact that a relatively great normal force can be applied, without causing any displacement of the test table in the normal direction and, at the same time, a slight lateral displacement of the test table is possible. In this connection, the amount of the displacement is precisely proportional to the deflection of the springs. Furthermore, both normal force and displacement and lateral force and displacement can be measured with great accuracy, independent of one another. In this connection, the accuracy that can be achieved is dependent on the sizing of the springs and the resolution of the measured-value transducers. Any slight normal bending of the system that remains can be detected and corrected by means of software.

Using the solution according to the invention in a nano-indenter makes it possible to precisely detect the start of crack formation or plastic deformation in the sample, and thereby to achieve quantitative data about mechanical characteristic values of the sample material. It is possible to achieve a resolution of the lateral displacement below 1 nm, and of the lateral force below 1 μm, using the new type of test table. Furthermore, it is possible, for the first time, to measure lateral forces and displacements that are exclusively caused by the normal force, and not by a lateral displacement of the sample holder or test body.

BRIEF DESCRIPTION OF THE DRAWINGS

The invention will be explained in greater detail in the following, using an exemplary embodiment.

The drawing shows.

DETAILED DESCRIPTION OF THE DRAWINGS

Figure 1:
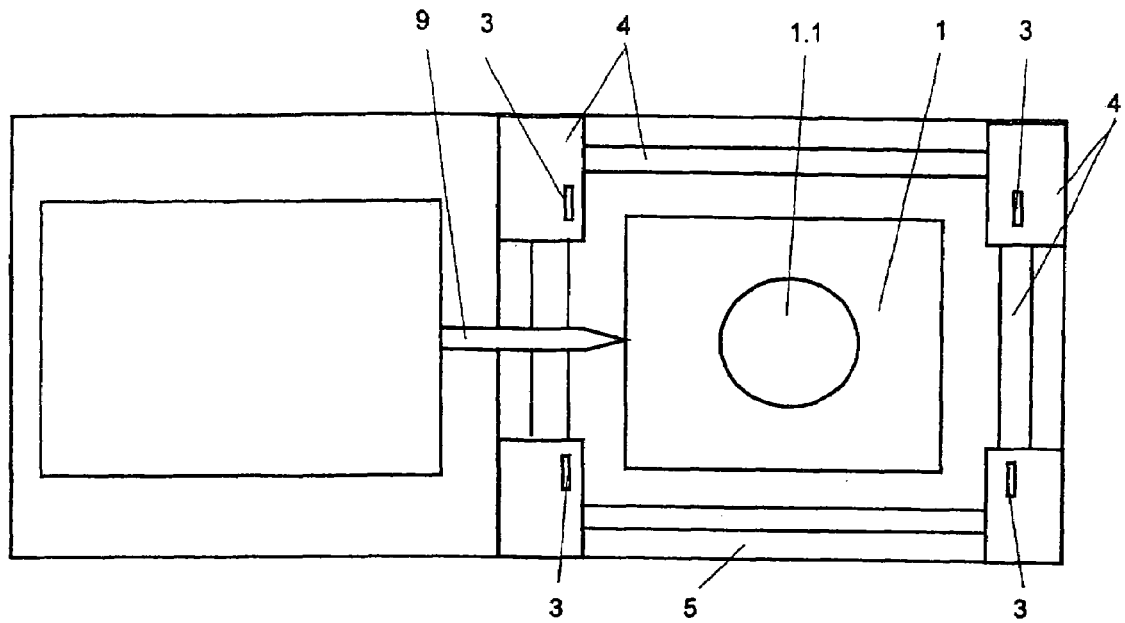
FIG. 1: fundamental representation in a top view.
Figure 2:
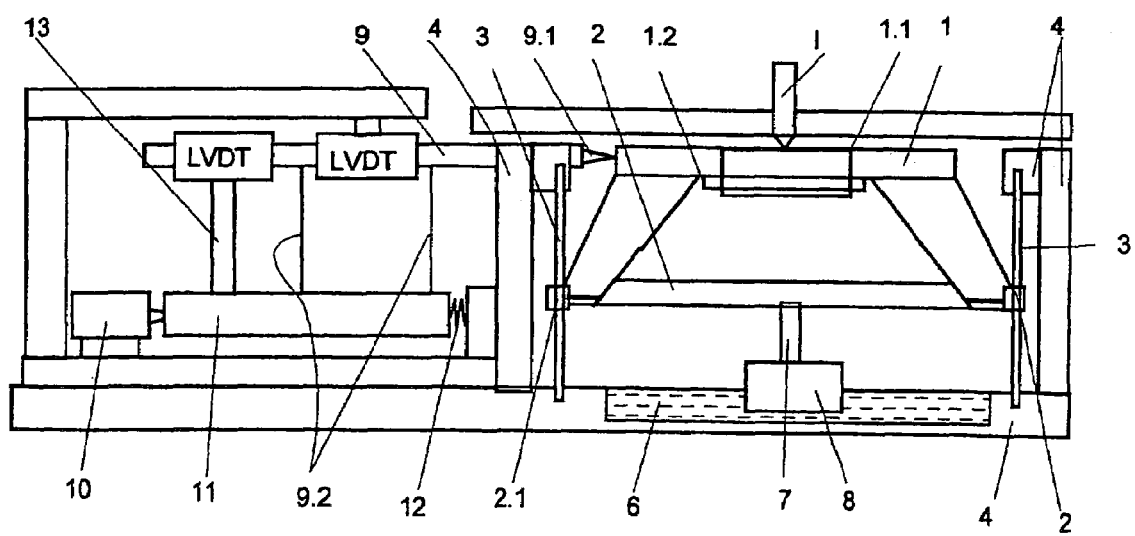
FIG. 2: fundamental representation in the front view according to FIG. 1.

According to FIGS. 1 and 2, the test table 1, with its vertically adjustable sample holder 1.1 (can be locked in place by means of a counter-nut 1.2), is attached to a total of four leaf springs 3 that stand perpendicular, by way of attachment elements 2.1 and longitudinal supports 2 that extend between the attachment elements 2.1. The four leaf springs 3 are attached between a frame 4 and a base plate S, under the effect of an axial bias, at their upper and at their lower ends, whereby the frame 4 sits on the base plate 5. There is an oil pan 6 in the base plate 5, into which a piston 8 attached to a piston rod 7 reaches from the underside of the test table 1, making it possible to achieve damping of the ambient vibrations. In the region vertically between two leaf springs 3 and the sample surface (not shown), and horizontally precisely in the center of the sample holder 1.1, a horizontal shaft 9 having a tip 9.1 is attached, according to FIG. 2, on which two LVDTs are provided and which serves to displace the table in the lateral direction and to measure the displacement with the LVDTs. In this connection, the shaft 9 is mounted on two spring elements 9.2, so as to be axially displaceable. The displacement of the table 1 relative to the leaf springs 3 is triggered using a piezo-element 10, which is connected with the LVDTs by way of a horizontal bar 11, which is supported on a spring 12, and by way of a perpendicular bar 13. The normal force is applied using an indenter I disposed above the test table 1.1.

Figure 3:
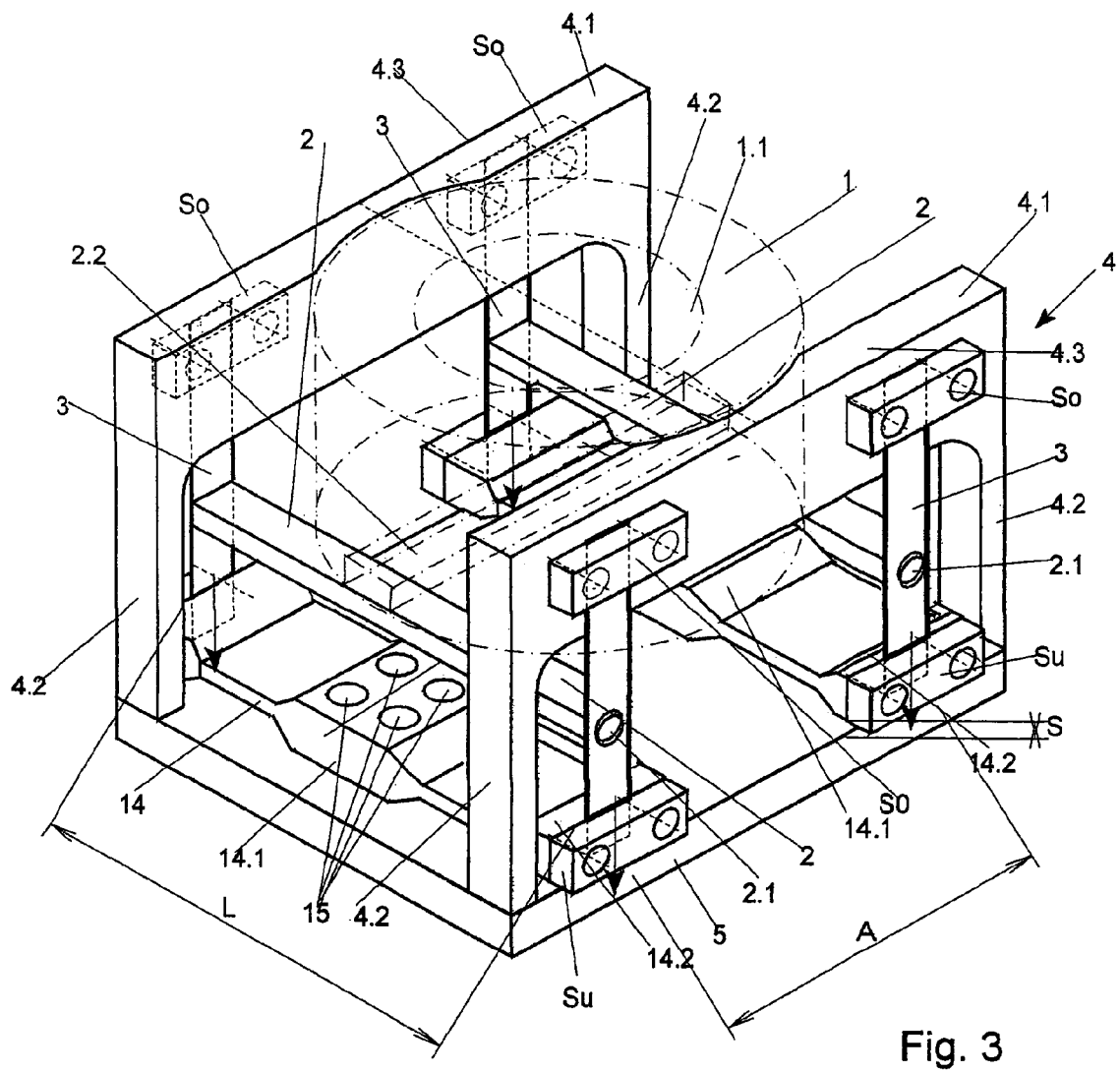
FIG. 3: three-dimensional fundamental representation of the attachment of the springs.

A three-dimensional fundamental representation of the attachment of the leaf springs 3 on the frame 4 and on the base plate 5 is shown in FIG. 3. The test table 1, with its sample holder 1.1, is merely indicated with a dot-dash line. It sits on two longitudinal supports 2, whereby each longitudinal support 2 is connected with a leaf spring 3 standing vertically, at its two ends, by way of attachment elements 2.1 that are merely indicated. The two longitudinal supports can additionally be reinforced with one another by way of a crosswise support 2.2 (or by way of a plate, not shown), on which the test table sits. The frame 4, which consists of two U-shaped supports 4.1, is disposed on the base plate 5. Each support 4.1 sits on the base plate 5 with two vertical shanks 4.2 that are parallel to one another; a horizontal shank 4.3 extends between the two vertical shanks 4.2 of a support 4.1. The upper ends of two leaf springs 3 are attached to each horizontal shank 4.3 of a support 4.1, by means of upper clamping jaws $S_o$.

Two solid body articulations 14 rest on the base plate 5 at their center 14.1, and are attached by means of screws 15, for example. The distance A between the solid body articulations 14 corresponds to the distance between two leaf springs 3 attached on a horizontal shank 4.3, the length L of each solid body articulation 14 corresponds to the distance between opposite leaf springs 3. Each leaf spring 3 is clamped in place at its lower end, at the corresponding end 14.2 of each solid body articulation 14, by way of lower clamping jaws $S_u$. The two ends 14.2 of each solid body articulation 14 are spaced apart from the base plate 5 by a gap S. Each end 14.2 of a solid body articulation 14 can be braced by way of bracing elements, not shown, which stand in engagement with the base plate 5 and the end 14.2 of the solid body articulation in the direction towards the base plate (direction of the arrow), thereby reducing the gap S and axially biasing the leaf springs 3.

The device for producing the lateral force and the normal force, the indenter, as well as the LVDTs and the oil damping, are not shown in FIG. 3.

As an alternative to the variant shown in FIG. 3, it is also possible to suspend the test table on only two or three leaf springs, or also on three or more leaf springs.

The invention claimed is:

1. Test table for measuring lateral forces and displacements, if necessary with the simultaneous use of normal forces, particularly in nano-indenters as well as in scratch and wear testers, whereby the test table is mounted to be laterally movable and the lateral force and displacement can be determined by way of measured-value acquisition, wherein the test table (1) is attached between at least two leaf springs (3) that stand perpendicular and can be deflected laterally in the direction of the lateral (horizontal) movement of the test table (1) that is to be produced, and the leaf springs (3) have a bias/tensile stress applied to them and are attached to a frame (4) at their lower end and at their upper end, and the table is essentially attached to a center of the leaf springs (3) between their lower end and their upper end.

2. Test table according to claim 1, wherein the test table (1) is suspended on the leaf springs (3) on a small surface as compared with the length of the leaf springs (3).

3. Test table according to claim 1, wherein two leaf springs (3), in each instance, stand opposite one another as a leaf spring pair.

4. Test table according to claim 1 wherein the test table (1) is disposed between several leaf spring pairs, disposed next to one another.

5. Test table according to claim 1, wherein the thickness of the leaf springs (3) is approximately greater than/equal to their lateral deflection.

6. Test table according to claim 1, wherein the test table (1) is connected to a damping unit.

7. Test table according to claim 6, wherein the damping unit is an oil bath (6) disposed below the test table (1), into which a damping element disposed on the test table (1) dips.

8. Test table according to claim 1, wherein the test table (1) has a sample holder (1.1) that is structured to be movable vertically.

9. Test table according to claim 1, wherein the measured-value acquisition to determine the lateral force and displacement comprises a shaft (9) that engages close to the sample.

10. Test table according to claim 1, wherein the measured-value acquisition to determine the lateral force and displacement takes place optically.

* * * * *